(12) United States Patent
Yang et al.

(10) Patent No.: US 11,452,716 B2
(45) Date of Patent: Sep. 27, 2022

(54) PHARMACEUTICAL COMPOSITION AND USE THEREOF

(71) Applicants: Ascentage Pharma (Suzhou) Co., Ltd., Suzhou (CN); Ascentage Pharma Group Corp Limited, Hong Kong (CN)

(72) Inventors: Dajun Yang, Suzhou (CN); Yifan Zhai, Suzhou (CN); Douglas Dong Fang, Suzhou (CN); Qiuqiong Tang, Suzhou (CN)

(73) Assignees: Ascentage Pharma (Suzhou) Co., Ltd., Suzhou (CN); Ascentage Pharma Group Corp Limited, Hong Kong (CN)

( * ) Notice: Subject to any disclaimer, the term of this patent is extended or adjusted under 35 U.S.C. 154(b) by 192 days.

(21) Appl. No.: 16/896,059

(22) Filed: Jun. 8, 2020

(65) Prior Publication Data
US 2020/0297704 A1 Sep. 24, 2020

Related U.S. Application Data

(63) Continuation of application No. PCT/CN2019/120155, filed on Nov. 22, 2019.

(30) Foreign Application Priority Data

Nov. 23, 2018 (WO) ............... PCT/CN2018/117271
Nov. 19, 2019 (CN) .......................... 201911132834.7

(51) Int. Cl.
*A61K 31/519* (2006.01)
*A61K 31/436* (2006.01)
*A61P 35/00* (2006.01)
*A61K 31/437* (2006.01)
*A61K 31/407* (2006.01)
*A61K 45/06* (2006.01)

(52) U.S. Cl.
CPC .......... *A61K 31/437* (2013.01); *A61K 31/407* (2013.01); *A61K 31/519* (2013.01); *A61K 45/06* (2013.01); *A61P 35/00* (2018.01)

(58) Field of Classification Search
CPC ...... A61K 31/519; A61K 31/436; A61P 35/00
See application file for complete search history.

(56) References Cited

U.S. PATENT DOCUMENTS

2015/0306104 A1 10/2015 Doshi et al.

FOREIGN PATENT DOCUMENTS

| CN | 104812414 A | 7/2015 |
| WO | WO 2015/097622 A1 | 7/2015 |
| WO | WO 2015/161032 A1 | 10/2015 |
| WO | WO 2017/176957 A1 | 10/2017 |
| WO | WO 2017/176958 A1 | 10/2017 |

*Primary Examiner* — Bruck Kifle
(74) *Attorney, Agent, or Firm* — Jones Day

(57) ABSTRACT

Disclosed is a pharmaceutical composition comprising (i) a compound of formula (I) or a pharmaceutically acceptable salt thereof; (ii) a CDK inhibitor or a pharmaceutically acceptable salt thereof, for the prevention and/or treatment of a disease mediated by MDM2 and/or CDK activity.

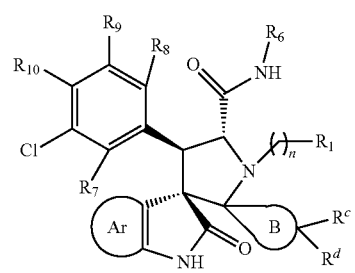

20 Claims, 3 Drawing Sheets

PHARMACEUTICAL COMPOSITION AND USE THEREOF

CROSS REFERENCE TO RELATED APPLICATIONS

This application is a continuation of International Application No. PCT/CN2019/120155, filed Nov. 22, 2019; which claims the benefit of Chinese Patent Application No. CN201911132834.7, filed Nov. 19, 2019, and International Application No. PCT/CN2018/117271, filed Nov. 23, 2018; the disclosure of each of which is incorporated herein by reference in its entirety.

FIELD OF INVENTION

The present invention relates to a novel pharmaceutical composition and a use thereof.

BACKGROUND OF THE INVENTION

TP53 (or p53) is a tumor suppressor that plays an important role in regulating cell cycles, apoptosis and preventing tumourigenesis when cells encounter environmental stress or genomic instability. TP53 is often mutated in many types of cancers, and in those bearing wild-type p53 gene, p53 could be inactivated by the amplification of MDM2, an E3 ligase mediating p53 protein degradation. Thus, inhibiting the interaction between TP53 and MDM2 can resume wild-type p53 function and becomes a new therapeutic target for cancer therapy.

Cyclin-dependent kinase 4 (CDK4) is a Ser/Thr protein kinase and is a member of the cyclin-dependent kinase family. CDK4 plays an important role in the G1-S phase. Considering the important function of CDK4 in the cell cycle, CDK4 gene amplification and overexpression very likely play important roles in tumourigenesis. Oral highly selective CDK inhibitors, including palbociclib, ribociclib, and abemaciclib, represent an important therapeutic advancement in oncology. But these inhibitors still have some disadvantages in treating cancer like dedifferentiated liposarcoma.

CONTENT OF THE INVENTION

In one aspect, the present invention provides a pharmaceutical composition comprising
(i) a compound of formula (I) or a pharmaceutically acceptable salt thereof; and,
(ii) a CDK inhibitor or a pharmaceutically acceptable salt thereof;

I wherein:

is selected from the group consisting of and ring B is a $C_{4-7}$ carbocyclic ring;

$R_1$ is H, substituted or unsubstituted $C_{1-4}$ alkyl, substituted or unsubstituted $C_{3-8}$ cycloalkyl, substituted or unsubstituted 4 to 12-membered heterocycloalkyl, $OR^a$, or $NR^aR^b$; the heteroatom of the heterocycloalkyl is independently selected from nitrogen, oxygen, and sulfur, the number of the heteroatom is 1-4;

n is 0, 1, or 2;

$R_2$, $R_3$, $R_4$, $R_5$, $R_7$, $R_8$, $R_9$, and $R_{10}$ are independently selected from the group consisting of H, F, Cl, $CH_3$, and $CF_3$;

$R_6$ is each of $R^a$ is independently H or substituted or unsubstituted $C_{1-4}$ alkyl;

each of $R^b$ is independently H or substituted or unsubstituted $C_{1-4}$ alkyl;

$R^c$ and $R^d$ are substituents on one carbon atom of ring B, wherein $R^c$ is H, $C_{1-3}$ alkyl, $C_{1-3}$ alkylene-$OR^a$, $OR^a$, or halo;

$R^d$ is H, $C_{1-3}$ alkyl, $C_{1-3}$ alkylene-$OR^a$, $OR^a$, or halo; or $R^c$ and $R^d$ are taken together with the carbon to which they are attached to form a 4 to 6-membered spiro substituent, optionally containing an oxygen atom; and $R^e$ is —C(=O)$OR^a$, —C(=O)$NR^aR^b$, or —C(=O)$NHSO_2CH_3$.

In some embodiments,

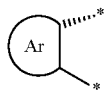

is

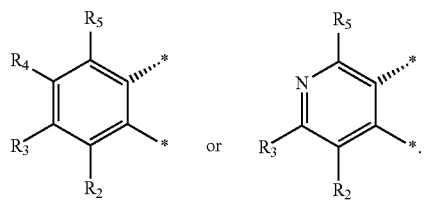

In some embodiments, ring B is

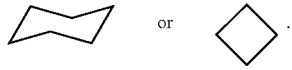

In some embodiments, ring B, $R^c$ and $R^d$ is

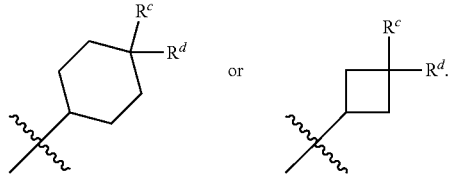

In some embodiments, $R^c$ and $R^d$ are independently H, halo, OH, $CH_3$, $CH_2CH_3$, or $CH_2OH$. In some embodiments, $R^c$ and $R^d$ are F and F; H and H; OH and $CH_3$; OH and H; $CH_3$ and $CH_3$; $CH_3$ and OH; H and OH; $CH_2CH_3$ and $CH_2CH_3$; or, $CH_2OH$ and $CH_2OH$.

In some embodiments, $R^c$ and $R^d$ are taken together with ring B to form a spiro moiety selected from the group consisting of

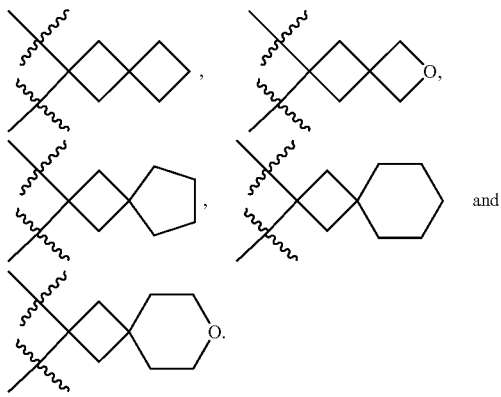

In some embodiments, $R^c$ and $R^d$ are taken together with ring B to form

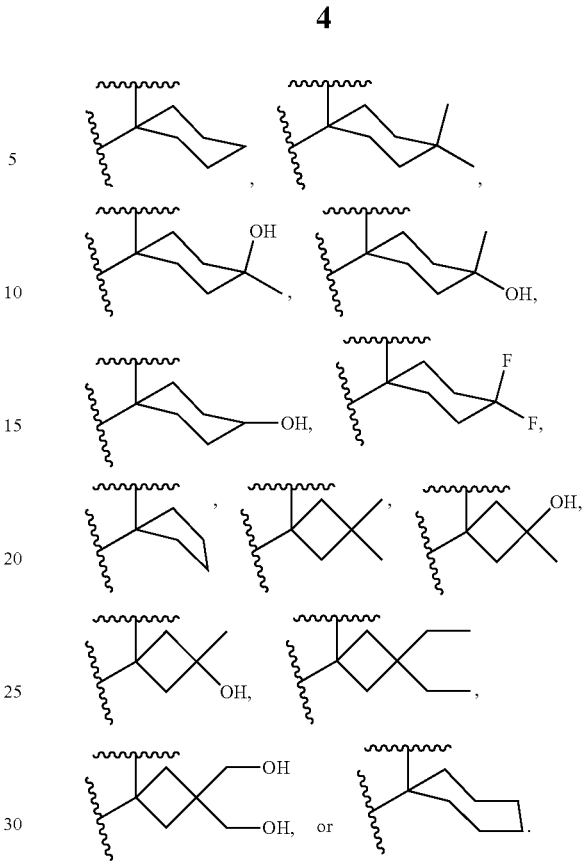

In some embodiments, $R^a$ and $R^b$ are independently H, $CH_3$, or $CH_2CH_3$.

In some embodiments, $R^6$ is

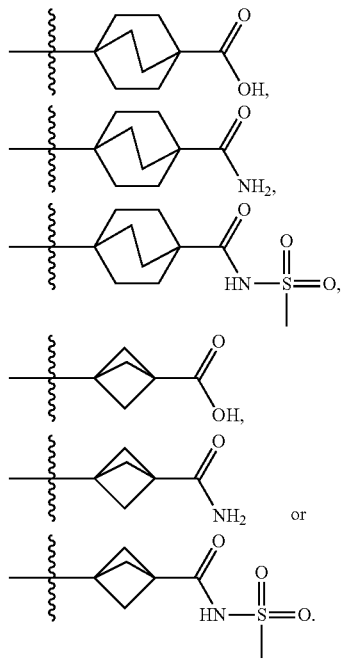

In some embodiments, n is 0 or 1. In some embodiments, $R_1$ is H or $CH_3$. In some embodiments,

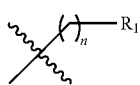

is H, CH$_3$, or CH$_2$CH$_3$.

In some embodiments, R$_2$ is H.

In some embodiments, R$_4$ is H. In some embodiments, R$_5$ is H. In some embodiments, R$_3$ is halo, preferably chloro.

In some embodiments, R$_4$ and R$_5$ are H.

In some embodiments, R$_7$ is fluoro.

In some embodiments, each of R$_8$, R$_9$, and R$_{10}$ is H.

In some embodiments, R$^e$ is —C(=O)OH, —C(=O)NH$_2$, or —C(=O)NHSO$_2$CH$_3$.

In some embodiments, the compound of formula (I) is selected from

Compound Q

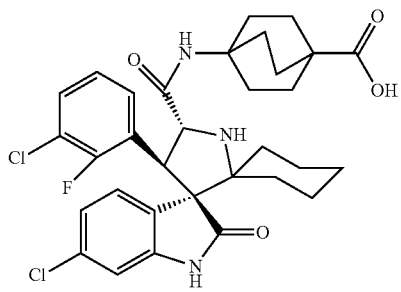

Compound M

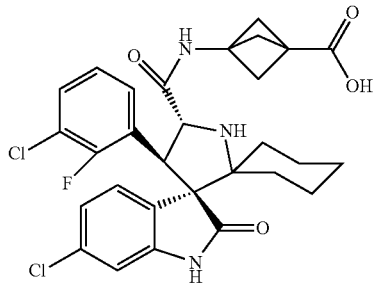

Compound N

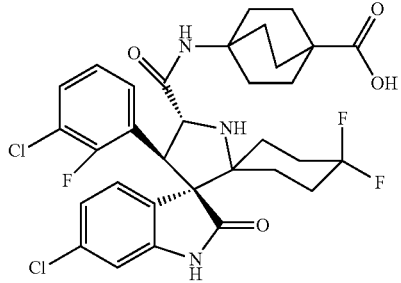

Compound H

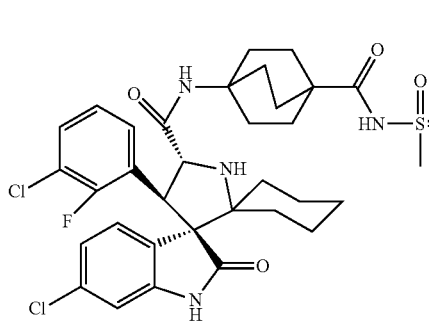

Compound J

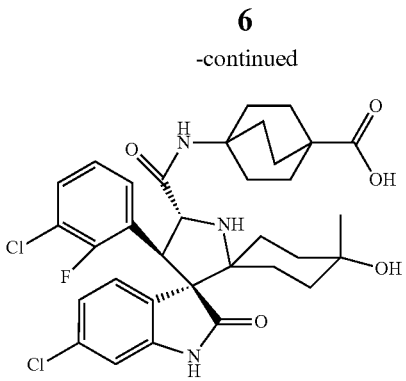

Compound G

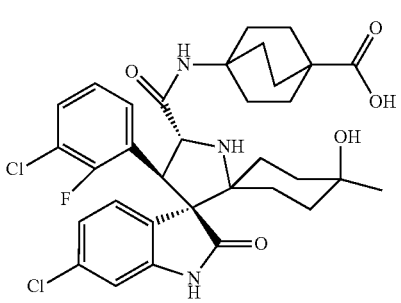

Compound E

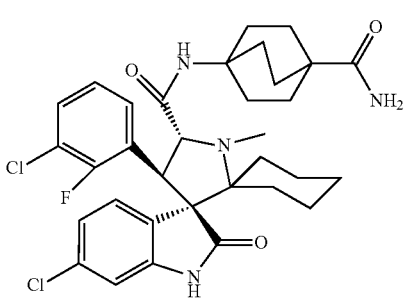

Compound C

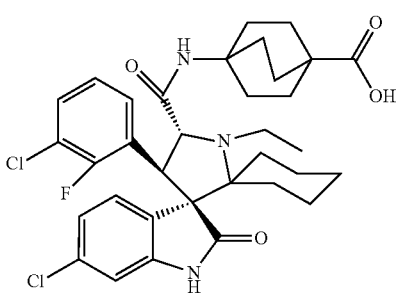

Compound F

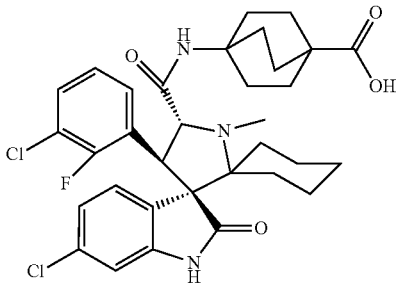

-continued

Compound Y

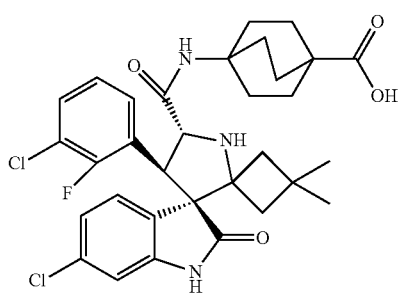

Compound K

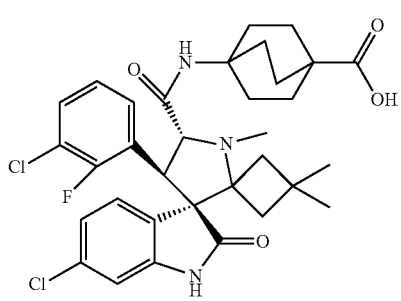

Compound P

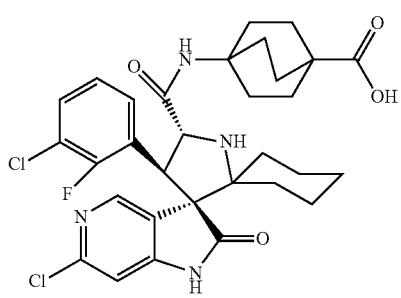

Compound T

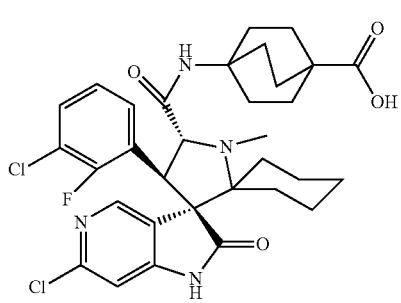

Compound S

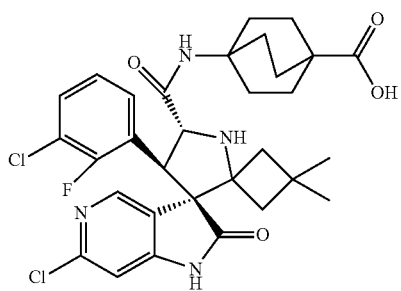

-continued

Compound W

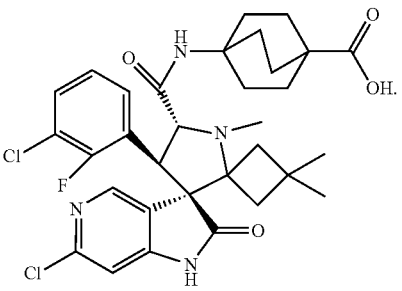

In some embodiments, the compound of formula (I) is

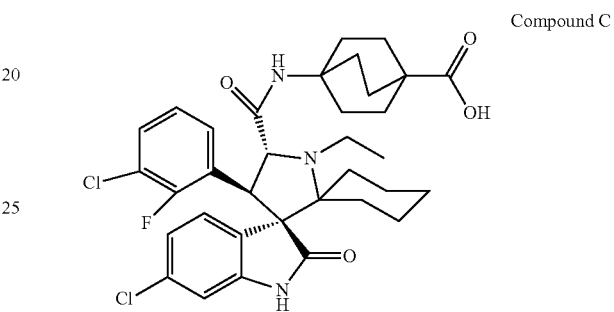

(the Chemical name is 4-((3'R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido)bicyclo[2.2.2]octane-1-carboxylic acid).

In another aspect, the present invention provides a pharmaceutical combination comprising
(i) a compound of formula (I) or a pharmaceutically acceptable salt thereof; and,
(ii) a CDK inhibitor or a pharmaceutically acceptable salt thereof.

In the above composition or combination, component (i) (i.e. the compound of formula (I)) and component (ii) (i.e. the CDK inhibitor) can be present in one combined unit dosage form or in two or more separate unit dosage forms. The unit dosage form may also be a fixed combination.

The present invention also provides a kit comprising in separate containers in a single package pharmaceutical compositions comprising a compound of formula (I) or a pharmaceutically acceptable salt thereof, and in a second container a pharmaceutical composition comprising a CDK inhibitor or a pharmaceutically acceptable salt thereof. The kit form is particularly advantageous when the separate components must be administered in different dosage forms (e.g. oral compound of formula (I) formulation and parenteral CDK inhibitor formulation) or are administered at different dosage intervals (e.g. the compound of formula (I) is administrated once every two days, while the CDK inhibitor is administrated daily).

In another aspect, the present invention provides a use of the pharmaceutical composition or combination according to the present invention in manufacturing a medicament for the prevention and/or treatment of a disease mediated by MDM2 and/or CDK activity.

In another aspect, the present invention provides a method for the prevention and/or treatment of a disease mediated by MDM2 and/or CDK activity, which comprises administering to a subject in need thereof a therapeutically effective amount of the pharmaceutical composition or combination according to the present invention. Each of the component of the composition or combination according to the present invention may be administered simultaneously or separately in any order.

In another aspect, the present invention provides a method for the prevention and/or treatment of a disease mediated by MDM2 and/or CDK activity, which comprises administering to a subject in need thereof a therapeutically effective amount of a compound of formula (I) or a pharmaceutically acceptable salt thereof, and a therapeutically effective amount of a CDK inhibitor or a pharmaceutically acceptable salt thereof. The compound of formula (I) and the CDK inhibitor may be administered simultaneously, sequentially or separately in any order.

The CDK inhibitor can be selected from the group consisting of kenpaullone, butyrolactone I, flavopiridol (alvocidib) (such as, flavopiridol hydrochloride), N9-isopropylolomoucine, indirubin-3'-monoxime, NU2058, olomoucine II, 9-cyanopaullone, 5-iodo-indirubin-3'-monoxime, NU6102, oxindole I, SU 9516, roscovitine, RO-3306, 10Z-hymenialdisine, AZD 5438, AT7519, AT7519 HCL, dinaciclib, R547, CGP 74514A, SNS-032 (BMS-387032), XL413 (BMS-863233), BMS-265246, JNJ-7706621, PHA-793887, P276-00, PHA-767491, milciclib (PHA-848125), NU6027, LDC000067, LDC4297 (LDC044297), MK-8776 (SCH 900776), Atuveciclib (BAY-1143572), Skp2 inhibitor C1 (SKPin C1), BS-181-HCL, THZ1 2HC1, Senexin A, MSC2530818, Wogonin, Purvalanol A, LY2857785, K03861, ML167, ON123300, ribociclib (Kisqali®), palbociclib (Ibrance®), and abemaciclib (Vernenio®).

In some embodiments, the CDK inhibitor is an inhibitor of CDK4 and/or CDK6, for example, compound A (also known as ribociclib) and/or compound B (also known as palbociclib):

Compound A

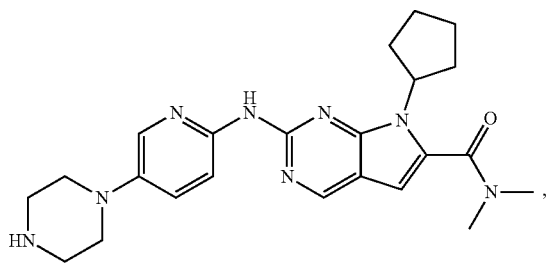

Compound B

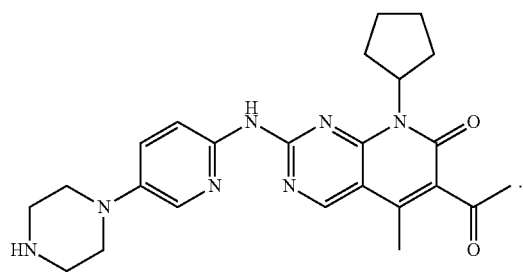

In some embodiments, the CDK inhibitor is the compound A or a pharmaceutically acceptable salt thereof.

In some embodiments, the CDK inhibitor is the compound B or a pharmaceutically acceptable salt thereof.

In some embodiments, the compound of formula (I) is the compound C or a pharmaceutically acceptable salt thereof, and the CDK inhibitor is compound A or a pharmaceutically acceptable salt thereof.

In some embodiments, the compound of formula (I) is the compound C or a pharmaceutically acceptable salt thereof, and the CDK inhibitor is compound B or a pharmaceutically acceptable salt thereof.

The disease mediated by MDM2 and/or CDK activity can be a cancer. The cancer includes, but is not limited to, adrenal cortical cancer, advanced cancer, anal cancer, aplastic anemia, bile duct cancer, bladder cancer, bone cancer, bone metastasis, brain/CNS tumors in adults, brain/CNS tumors in children, breast cancer, breast cancer in men, cancer in children, cancer of unknown primary, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal and hypopharyngeal cancer, leukemia-acute lymphocytic (ALL) in adults, leukemia-acute myeloid (AML), leukemia-chronic lymphocytic (CLL), leukemia-chronic myeloid (CML), leukemia-chronic myelomonocytic (CMML), leukemia in children, liver cancer, lung cancer-non-small cell, lung cancer-small cell, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, non-Hodgkin lymphoma in children, oral cavity and oropharyngeal cancer, osteosarcoma, liposarcoma (e.g. well-differentiated liposarcoma or dedifferentiated liposarcoma), leiomyosarcoma, alveolar and embryonal rhabdomyosarcoma, ovarian cancer, pancreatic cancer, penile cancer, pituitary tumors, prostate cancer, retinoblastoma, rhabdomyosarcoma, salivary gland cancer, sarcoma-adult soft tissue cancer, skin cancer-basal and squamous cell, skin cancer-melanoma, small intestine cancer, stomach cancer, testicular cancer, thymus cancer, thyroid cancer, uterine sarcoma, vaginal cancer, vulvar cancer, Waldenstrom macroglobulinemia, and Wilms Tumor.

In some embodiments, the disease mediated by MDM2 and/or CDK activity is leiomyosarcoma, alveolar and embryonal rhabdomyosarcoma, well-differentiated liposarcoma or dedifferentiated liposarcoma. In some embodiments, the disease mediated by MDM2 and/or CDK activity is dedifferentiated liposarcoma. In some embodiments, the disease mediated by MDM2 and/or CDK activity is well-differentiated liposarcoma.

The present invention also provides a method for the prevention and/or treatment of a cancer, which comprises administering to a subject in need thereof a therapeutically effective amount of a compound of formula (I) or a pharmaceutically acceptable salt thereof, and a therapeutically effective amount of a CDK inhibitor or a pharmaceutically acceptable salt thereof. The cancer includes, but is not limited to, adrenal cortical cancer, advanced cancer, anal cancer, aplastic anemia, bile duct cancer, bladder cancer, bone cancer, bone metastasis, brain/CNS tumors in adults, brain/CNS tumors in children, breast cancer, breast cancer in men, cancer in children, cancer of unknown primary, Castleman disease, cervical cancer, colon/rectum cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal and hypopharyngeal cancer, leukemia-acute lymphocytic (ALL) in adults, leukemia-acute myeloid (AML), leukemia-chronic lymphocytic (CLL), leukemia-chronic myeloid (CML), leukemia-chronic myelomonocytic (CMML), leukemia in children, liver cancer, lung cancer-non-small cell, lung cancer-small cell, lung carcinoid tumor, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, non-Hodgkin lymphoma in children, oral cavity and oropharyngeal cancer, osteosarcoma, liposarcoma (e.g. well-differentiated liposarcoma or dedifferentiated liposarcoma), leiomyosarcoma, alveolar and embryonal rhabdomyosarcoma, ovarian cancer, pancreatic cancer, penile cancer, pituitary tumors, prostate cancer, retinoblastoma, rhabdomyosarcoma, salivary gland cancer, sarcoma-adult soft tissue cancer, skin cancer-basal and squamous cell, skin cancer-melanoma, small intestine cancer, stomach cancer, testicular cancer, thymus cancer, thyroid cancer, uterine sarcoma, vaginal cancer, vulvar cancer, Waldenstrom macroglobulinemia, and Wilms Tumor. In some embodiments, the cancer is leiomyosarcoma, alveolar and embryonal rhabdomyosarcoma, well-differentiated liposarcoma or dedifferentiated liposarcoma. In some embodiments, the cancer is dedifferentiated liposarcoma. In some embodiments, the cancer is well-differentiated liposarcoma.

The pharmaceutical composition or combination according to the present invention can further comprises a pharmaceutical carrier.

In the above composition or combination, the weight ratio of the compound of formula (I) to the CDK inhibitor can be 50:1 to 1:50, e.g. 50:1, 45:1, 40:1, 35:1, 30:1, 25:1, 20:1, 15:1, 10:1, 9:1, 8:1, 7:1, 6:1, 5:1, 4:1, 3:1, 2:1, 0.8:1, 1:1, 1.6:1, 8:15, 1:2, 1:3, 1:4, 1:5, 1:6, 1:7, 1:8, 1:9, 1:10, 1:15, 1:20, 1:25, 1:30, 1:35, 1:40, 1:45 or 1:50.

A therapeutically effective amount of the compound of formula (I) and the CDK inhibitor can be administered to a subject in a weight ratio of 50:1 to 1:50, e.g. 50:1, 45:1, 40:1, 35:1, 30:1, 25:1, 20:1, 15:1, 10:1, 9:1, 8:1, 7:1, 6:1, 5:1, 4:1, 3:1, 2:1, 0.8:1, 1:1, 1.6:1, 8:15, 1:2, 1:3, 1:4, 1:5, 1:6, 1:7, 1:8, 1:9, 1:10, 1:15, 1:20, 1:25, 1:30, 1:35, 1:40, 1:45 or 1:50.

In some embodiments, the compound of formula (I), e.g. the compound C, and the CDK inhibitor, e.g. palbociclib, can be administered to a subject in a weight ratio of 1.6:1. In some embodiments, the compound of formula (I) and the CDK inhibitor, e.g. palbociclib, can be administered to a subject in a weight ratio of 0.8:1. In some embodiments, the compound of formula (I) (e.g. the compound C) and the CDK inhibitor (e.g. palbociclib) can be administered to a subject in a weight ratio of 2:1.

In some embodiments, the compound of formula (I), e.g. the compound C, and the CDK inhibitor, e.g. ribociclib, can be administered to a subject in a weight ratio of 8:15.

Preferred dosages for the compounds of the present invention are therapeutically effective dosages, especially those which are commercially available.

A "therapeutically effective amount" of a compound or a composition refers to an amount sufficient to cure, alleviate or partially arrest the clinical manifestations of a given disease or disorder and its complications. The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or clinical scientist. It will be appreciated that the unit content of each active agent contained in an individual dose of each dosage form need not in itself constitute an effective amount since the necessary effective amount can be reached by administration of a plurality of dosage units.

For example, the compound of formula (I) as part of the composition or combination according to the present invention may be orally administered to a subject at a dose of 1-1000 mg, e.g. 1, 5, 10, 15, 20, 25, 30, 35, 40, 45, 50, 55, 60, 65, 70, 75, 80, 85, 90, 95, 100, 125, 150, 175, 200. 225, 250, 275, 300, 325, 350, 375, 400, 425, 450, 475 or 500 mg. In some embodiments, the compound of formula (I), e.g. the compound C, as part of the composition or combination according to the present invention may be orally administered to a subject, e.g. a human, at a dose of 1-500 mg, e.g. 1-200 mg, e.g. 100-200 mg, e.g. 150-200 mg. These doses may be administered once, twice or three times daily. These doses may also be administered once every two days. For example, the compound of formula (I) can be orally administered to a subject once every two days at a dose of 1-500 mg, e.g. 1-200 mg, e.g. 100-200 mg, e.g. 150-200 mg.

For example, a CDK inhibitor, e.g. the compound A or the compound B, as part of the composition or combination according to the present invention, may be orally administered to a subject at a dose of 0.1-1000 mg, e.g. 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95, 100, 125, 150, 175, 200. 225, 250, 275, 300, 325, 350, 375, 400, 425, 450, 475 or 500 mg. These doses may be administered once, twice or three times daily. For example, a CDK inhibitor, e.g. the compound A or the compound B, can be orally administered once daily.

The compound of formula (I) has been disclosed in WO2015161032A1, which is incorporated herein by reference in its entirety.

The compound of formula (I) and the CDK inhibitor may be administered simultaneously or separately in any order. By "simultaneously", it is meant that all agents are administered at a same time point. However, if not administered simultaneously, it is meant that they are administered to a subject in a sequence and sufficiently close in time so as to provide the desired therapeutic effect and can act in concert. For example, a CDK inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the compound of formula (I), to a subject in need thereof. In various embodiments, a CDK inhibitor and the compound of formula (I) are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart.

The compounds of the present invention may be administered orally. Oral administration may involve swallowing, so that the compound enters the gastrointestinal tract, and/or buccal, lingual, or sublingual administration by which the compound enters the blood stream directly from the mouth. For example, the compound of formula (I) can be administered orally. For example, the CDK inhibitor, e.g. the compound A or the compound B, can be administered orally.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches. Further, the compound or salts of the invention can be administered as a spray dried dispersion. Solid formulations for oral administration may be formulated to be immediate and/or modified release. Modified release formulations include delayed-, sustained-, pulsed-, controlled-, targeted and programmed release.

Liquid formulations include suspensions, solutions, syrups and elixirs. Such formulations may be employed as fillers in soft or hard capsules (made, for example, from gelatin or hydroxypropyl methylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the present invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Formulations for parenteral administration may be formulated to be immediate and/or modified release. Modified release formulations include delayed-, sustained-, pulsed-, controlled-, targeted and programmed release. Thus the compounds of the prevent invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic) acid (PGLA) microspheres.

The compounds of the present invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, *J Pharm Sci,* 88 (10), 955-958, by Finnin and Morgan (October 1999).

Formulations for topical administration may be formulated to be immediate and/or modified release. Modified release formulations include delayed-, sustained-, pulsed-, controlled-, targeted and programmed release.

The term "carrier" refers to a diluent, adjuvant, excipient, or vehicle with which the compound is administered. Suitable pharmaceutical carriers are described in "Remington's Pharmaceutical Sciences" by E. W. Martin. Typical pharmaceutically carriers for use are exemplified by: sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene glycol polymers; betacyclodextrin; fatty alcohols; and hydrolyzed cereal solids, as well as other non-toxic compatible fillers, binders, disintegrants, buffers, preservatives, antioxidants, lubricants, flavoring agents, and the like commonly used in pharmaceutical formulations.

The term "pharmaceutical combination" is used herein to mean a product including the active ingredients (e.g. the compound C, the CDK inhibitor) according to the present invention. The active ingredients included by the pharmaceutical combination can be present in a single entity (e.g., a single dosage form, e.g., in one injection, in one tablet or in one capsule), and thus can be administered to a subject simultaneously. The active ingredients included by the pharmaceutical combination can also be present in separate entities (e.g., one active ingredient is present in an tablet, while the other active ingredient is present in a capsule), and thus can be administered to a subject independently of each other, either simultaneously or separately with no specific time limits. If the active ingredients included by the pharmaceutical combination are present in separate entities, they can be sold independently of each other and just instruction of the possibility of their combined use is provided in the package equipment, e.g., leaflet or the like, or in other information, e.g., provided to physicians and medical staff (e.g., oral communications).

The term "combination" is used herein to mean either, simultaneous administration or any manner of separate sequential administration of a therapeutically effective amount of the compound of formula (I) and a CDK inhibitor or a pharmaceutically acceptable salt thereof. Preferably, if the administration is not simultaneous, the compounds are administered in a close time proximity to each other. Furthermore, it does not matter if the compounds are administered in the same dosage form, e.g. one compound may be administered topically and the other compound may be administered orally. Suitably, both compounds are administered orally.

The term "synergistic", as used herein, means that the effect achieved with the methods, combinations and compositions of the present invention is greater than the sum of the effects that result from individual methods and compositions comprising the active ingredients of this invention separately. The "synergistic" effect of a combination is determined herein by the methods described in Clarke R. Issues in experimental design and endpoint analysis in the study of experimental cytotoxic agents in vivo in breast cancer and other models[J]. *Breast Cancer Research & Treatment,* 1997, 46(2-3):255-278, which is incorporated herein by reference in its entirety. See also Gould S E et al. Translational value of mouse models in oncology drug development. *Nature medicine.* 2015 21, 431-439, which is incorporated herein by reference in its entirety.

The term "pharmaceutically acceptable salt" refers to a non-toxic salt commonly used in the pharmaceutical industry which may be prepared according to methods well-known in the art.

The term "pharmaceutically acceptable", as used herein, refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

The term "prevention" refers to prophylactic administration to healthy patients to prevent the development of the conditions mentioned herein. Moreover, the term "prevention" means prophylactic administration to patients being in a pre-stage of the conditions to be treated.

The term "treatment" is understood the management and care of a patient for the purpose of combating the disease, condition or disorder.

The term "subject" refers to any animal, including mammals, such as mice, rats, other rodents, rabbits, dogs, cats, pigs, cattle, sheep, horses, primates, or humans. The preferred subjects are humans.

The term "CDK" is an abbreviation of "cyclic-dependent kinase", which refers to a family of proteins capable of complexing with a cyclin and capable of catalyzing phosphorylation of a substrate. Cyclin-dependent kinases (also called CDKs) are known in the art and include, for example, CDK1, CDK2, CDK3, CDK4, CDK5, CDK6, CDK7, CDK8, and CDK9.

The term "CDK inhibitor" refers to any compound that reduces, or inhibits, either partially or in full, the activity of a CDK. A CDK inhibitor may directly or indirectly reduce or inhibit the activity of one or more specific CDK(s). For example, an inhibitor of CDK4 and CDK6 can simultaneously inhibit the activity of CDK4 and CDK6.

The term "disease mediated by MDM2" refers to a disease in which activity of MDM2 leads to abnormal activity of the regulatory pathways including overexpression, mutation or relative lack of activity of other regulatory pathways in the cell that result in excessive cell proliferation, e.g. cancer.

The term "disease mediated by CDK" refers to a disease in which activity of CDK leads to abnormal activity of the regulatory pathways including overexpression, mutation or relative lack of activity of other regulatory pathways in the cell that result in excessive cell proliferation, e.g. cancer.

The term "container" means any receptacle and closure therefor suitable for storing, shipping, dispensing, and/or handling a pharmaceutical product.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

The pharmaceutical compositions and preparations can be manufactured by conventional mixing, granulating, dragee-making, dissolving, or lyophilizing processes.

The compounds of the present invention can be present as pharmaceutical acceptable salts. If these compounds have, for example, at least one basic center, they can form acid addition salts. Corresponding acid addition salts can also be formed having, if desired, an additionally present basic center. The compounds having at least one acid group (for example COOH) can also form salts with bases. Corresponding internal salts may furthermore be formed, if a compound comprises e.g. both a carboxy and an amino group.

The compounds of the present invention can be present in form of a hydrate or include other solvents used for crystallization.

The compounds of the present invention can be present in form of one or more polymorphic forms.

The present invention further includes all possible stereoisomers and geometric isomers of the compounds of the present invention. The present invention includes both racemic compounds and optically active isomers. When a compound is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

The present invention includes all pharmaceutically acceptable isotopically-labeled compounds, e.g. compound of formula (I), wherein one or more atoms are replaced by atoms having the same atomic number, but an atomic mass or mass number different from the atomic mass or mass number usually found in nature.

Examples of isotopes suitable for inclusion in the compounds of the present invention comprises isotopes of hydrogen, such as $^2$H and $^3$H, carbon, such as $^{11}$C, $^{13}$C and $^{14}$C, nitrogen, such as $^{13}$N and $^{15}$N, oxygen, such as $^{15}$O, $^{17}$O and $^{18}$O.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

The compounds of the present invention can be present as prodrugs. Thus, certain derivatives which may have little or no pharmacological activity themselves can, when administered into or onto the body, be converted into compounds of the present invention having the desired activity, for example, by hydrolytic cleavage. Such derivatives are referred to as 'prodrugs'. Further information on the use of prodrugs may be found in 'Pro-drugs as Novel Delivery Systems, Vol. 14, *ACS Symposium Series* (T Higuchi and W Stella) and 'Bioreversible Carriers in Drug Design', *Pergamon Press,* 1987 (ed. E B Roche, American Pharmaceutical Association).

Prodrugs can, for example, be produced by replacing appropriate functionalities present in the compounds of the present invention with certain moieties known to those skilled in the art as 'pro-moieties' as described, for example, in "Design of Prodrugs" by H Bundgaard (Elsevier, 1985).

Some examples of such prodrugs include:

(i) where the compound contains an alcohol functionality (—OH), an ether thereof, for example, replacement of the hydrogen with ($C_1$-$C_6$)alkanoyloxymethyl;

(ii) where the compound contains a secondary amino functionality, an amide thereof, for example, replacement of hydrogen with ($C_1$-$C_{10}$)alkanoy.

As used herein, the term "alkyl" refers to straight chained and branched saturated hydrocarbon groups, including but not limited to methyl, ethyl, n-propyl, propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term Cm-n means the alkyl group has "m" to "n" carbon atoms. The term "alkylene" refers to an alkyl group having a substituent. An alkyl, e.g., methyl, or alkylene, e.g., —$CH_2$—, can be substituted with one or more, and typically one to three, of the group independently selected from halo, trifluoromethyl, trifluoromethoxy, hydroxy, alkoxy, nitro, cyano, alkylamino, and amino groups.

As used herein, the term "halo" is defined as fluoro, chloro, bromo, and iodo.

The term "hydroxy" is defined as —OH.

The term "alkoxy" is defined as —OR, wherein R is alkyl.

The term "amino" is defined as —$NH_2$, and the term "alkylamino" is defined as —NR2, wherein at least one R is alkyl and the second R is alkyl or hydrogen.

The term "carbamoyl" is defined as —C(=O)$NR_2$.

The term "carbamoyl" is defined as —C(=O)$NR_2$.

The term "nitro" is defined as —$NO_2$.

The term "cyano" is defined as —CN.

The term "trifluoromethyl" is defined as —$CF_3$.

The term "trifluoromethoxy" is defined as —$OCF_3$.

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, of the group independently selected from, for example, halo, alkyl, alkenyl, —$OCF_3$, —$NO_2$, —CN, —NC, —OH, alkoxy, amino, alkylamino, —$CO_2H$, —$CO_2$alkyl, —OCOalkyl, aryl, and heteroaryl.

As used herein, the term "heterocyclic" refers to a heteroaryl and heterocycloalkyl ring systems.

As used herein, the term "heteroaryl" refers to a monocyclic or bicyclic ring system containing one or two aromatic rings and containing at least one nitrogen, oxygen, or sulfur atom in an aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl group has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four, of the group independently selected from, for example, halo, alkyl, alkenyl, —$OCF_3$, —$NO_2$, —CN, —NC, —OH, alkoxy, amino, alkylamino, —$CO_2H$, —$CO_2$alkyl, —OCOalkyl, aryl, and heteroaryl.

As used herein, the term "cycloalkyl" means a monocyclic or bicyclic, saturated or partially unsaturated, ring system containing three to eight carbon atoms, including cyclopropyl, cyclobutyl, cyclopentyl, cyclohexyl, cycloheptyl, and cyclooctyl, optionally substituted with one or more, and typically one to three, of the group independently selected from halo, trifluoromethyl, trifluoromethoxy, hydroxy, alkoxy, nitro, cyano, alkylamino, or amino groups.

As used herein, the term "heterocycloalkyl" means a monocyclic or a bicyclic, saturated or partially unsaturated, ring system containing 4 to 12 total atoms, of which one to five of the atoms are independently selected from nitrogen, oxygen, and sulfur and the remaining atoms are carbon. Nonlimiting examples of heterocycloalkyl groups are azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, diazacycloheptyl, each optionally substituted with one or more, and typically one to three, of the group independently selected from halo, $C_{1-6}$ alkyl, $C_{1-6}$ alkoxy, cyano, amino, carbamoyl, nitro, carboxy, $C_{2-7}$ alkenyl, $C_{2-7}$ alkynyl, and the like on an atom of the ring.

The abbreviations "p.o" (i.e. orally), "q.d" or "QD" (i.e. daily), "q.2d" or "Q2D" (i.e. once every two days) and the like are used to describe the route of administration or the dosage regiment in their general meanings.

All publications and patent applications mentioned herein are herein incorporated by reference in their entireties to the same extent as if each individual publication or patent application is specifically and individually indicated to be incorporated by reference.

The person skilled in the pertinent art is fully enabled to select a relevant test model to prove the efficacy of the composition of the present invention in the hereinbefore and hereinafter indicated therapeutic indications. Representative studies are carried out with a combination of the compound of formula (I) and palbociclib or ribociclib.

It has surprisingly been found that, a combination of the compound C and palbociclib achieves greater therapeutic effect than the administration of the compound C or palbociclib alone and significantly reduces the tumor growth and increase the response rate in a liposarcoma patient-derived xenograft model, which exhibits a significant synergistic effect.

Further benefits can be that lower doses of the individual drugs to be combined according to the present invention can be used to reduce the dosage, for example, that the dosages need not only often be smaller but are also applied less frequently, or can be used to diminish the incidence of side effects.

DETAILED DESCRIPTION OF THE PREFERRED EMBODIMENT

Figure 1:
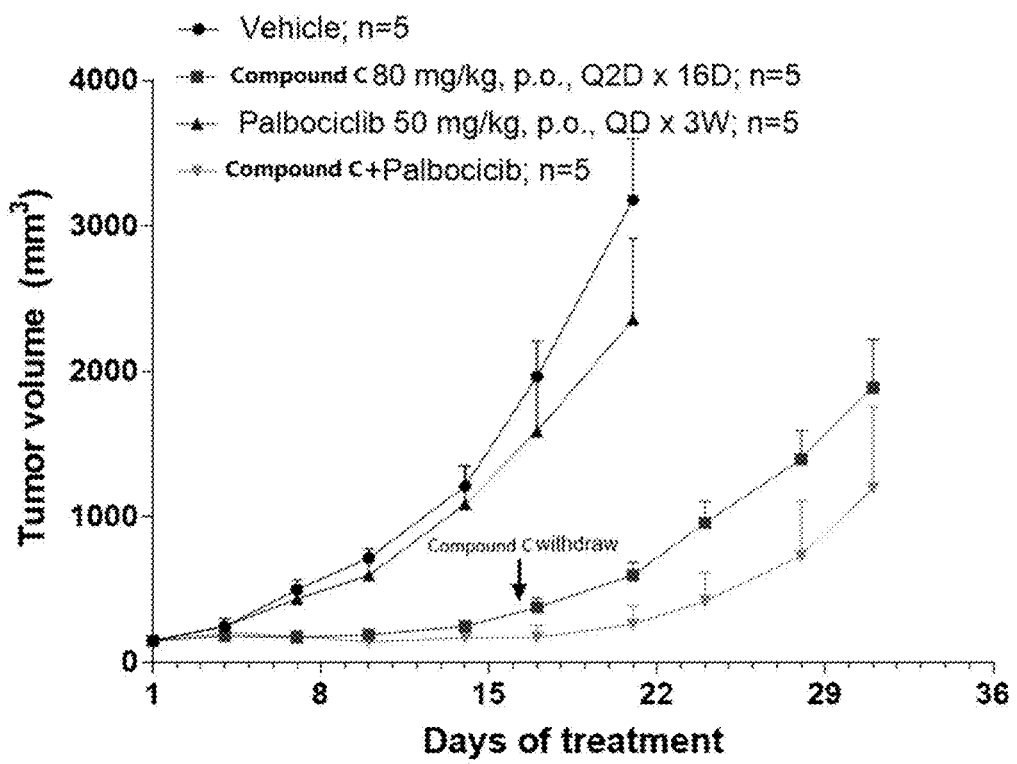
FIG. 1 shows antitumor activity of compound C as a single agent or in combination with palbociclib in the treatment of liposarcoma patient derived xenograft (Mean±SEM) in embodiment 2.

The following examples further illustrate the present invention, but the present invention is not limited thereto.

Embodiment 1 Synthesis of Compound C

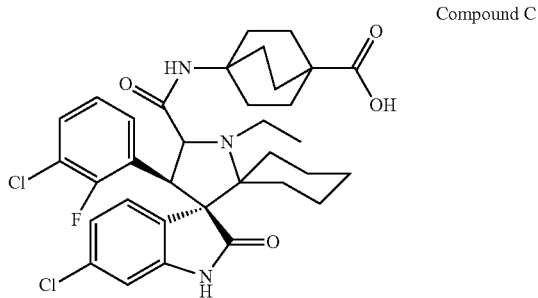 [SMILES: CCN1C(C(=O)NC23CCC(C(=O)O)(CC2)CC3)[C@H](c2cccc(Cl)c2F)[C@]2(C(=O)Nc3cc(Cl)ccc32)C12CCCCC2]

Compound C

Compound C was synthesized according to WO2015161032A1.

Embodiment 2: Antitumor Activity of Compound C as a Single Agent or in Combination with Palbociclib in the Treatment of Liposarcoma Patient Derived Xenograft Animals: Balb/c nude, female, 6-8 weeks, weighing approximately 18-22 g. A total of 40 (20 plus 100%) will be needed for the study, which will be purchased from Shanghai SLAC Laboratory Animal Co., LTD.

Generation of the subcutaneous liposarcoma patient-derived xenograft (LP-19-0029 PDX) Model: The LP-19-0029 PDX model was originally established from a surgically resected clinical sample (cancer type: liposarcoma; pathology diagnosis: dedifferentiated liposarcoma), and implanted in nude mice defined as passage 0 (P0). The next passage implanted from P0 tumor was defined as passage 1 (P1), and so on during continual implantation in mice. The frozen tumor fragments will be revived in NOD SCID mice, when the tumors develop to suitable size, they will be passaged to Balb/c nude mice. The P4-P7 tumors will be used for the study.

Tumor Implantation and Animal Grouping

Each mouse was implanted subcutaneously at the right flank with the LP-19-0029 P4 tumor slices (about 30 mm$^3$) for tumor development. Treatments were started when the average tumor size reached approximately 150 mm$^3$. The animals were assigned into groups using an Excel-based randomization software performing stratified randomization based upon their tumor volumes. Each group consisted of 5 tumor-bearing mice. The testing article was administrated to the mice according to the predetermined regimen as shown in Table 1.

TABLE 1

| | | | | Dosing | | |
|---|---|---|---|---|---|---|
| | | | Dose | Volume | Dosing | |
| Group | n | Treatment | (mg/kg) | (μL/g) | Route | Schedule |
| 1 | 5 | Compound C vehicle + Palbociclib vehicle | — | 10 + 10 | p.o. + p.o. | Q2D + QD |
| 2 | 5 | Compound C | 80 | 10 | p.o. | Q2D × 16D |
| 3 | 5 | Palbociclib | 50 | 10 | p.o. | QD × 3W |
| 4 | 5 | Compound C + Palbociclib | 80 + 50 | 10 + 10 | p.o. + p.o. | Q2D + QD |

Note:
n: animal number;
Dosing volume: adjust dosing volume based on body weight 10 μL/g.
Treatment schedule may be adjusted if body weight loss >15%.
Q2D: once every two days;
QD: daily;
p.o.: orally.

Observations

All the procedures related to animal handling, care and the treatment in the study were performed according to the guidelines approved by the Institutional Animal Care and Use Committee (IACUC) of WuXi AppTec following the guidance of the Association for Assessment and Accreditation of Laboratory Animal Care (AAALAC). At the time of routine monitoring, the animals were daily checked for any effects of tumor growth and treatments on normal behavior such as mobility, food and water consumption (by looking only), body weight gain/loss (body weights were measured twice weekly), eye/hair matting and any other abnormal effect as stated in the protocol. Death and observed clinical signs were recorded on the basis of the numbers of animals within each subset.

Tumor Measurements and Endpoints

After tumor inoculation, the animals were checked daily for morbidity and mortality. At the time of routine monitoring, the animals were checked for any effects of tumor growth and treatments on normal behavior such as mobility, visual estimation of food and water consumption, body weight gain/loss (body weights were measured twice weekly), eye/hair matting and any other abnormal effect. Death and observed clinical signs were recorded on the basis of the numbers of animals within each subset. The entire procedures of dosing as well as tumor and body weight measurement were conducted in a Laminar Flow Cabinet.

Tumor volumes were measured twice weekly in two dimensions using a caliper, and the volume was expressed in mm$^3$ using the formula:

Tumor Volume($mm^3$)=0.5a×b$^2$ where a and b are the long and short diameters of the tumor, respectively.

Relative tumor volume (RTV) was calculated using the following formula:

$$RTV = V_t/V_1$$

where $V_1$ and $V_t$ are the average tumor volumes on the first day of treatment (day 1) and the average tumor volumes on a certain time point (day t).

Synergy score was calculated using the following formula described in Clarke R. Issues in experimental design and endpoint analysis in the study of experimental cytotoxic agents in vivo in breast cancer and other models[J]. *Breast Cancer Research & Treatment*, 1997, 46(2-3):255-278, which is incorporated by reference in its entirety:

Synergy score=((A/C)×(B/C))/(AB/C);

where A is RTV value of drug A; B is RTV value of drug B; C is RTV value of vehicle control. AB is RTV value of combination treatment with A and B. Synergy scores: >1 represents synergistic, =1 represents additive, <1 represents antagonistic (referring to Gould S E et al. Translational value of mouse models in oncology drug development. *Nature medicine*. 2015 21, 431-439).

Standard NCI procedures were used to calculate tumor parameters. Percent tumor growth inhibition (% T/C) was calculated as the mean RTV of treated tumors (T) divided by the mean RTV of control tumors (C)×100%. The percentage T/C value is an indication of antitumor effectiveness: a value of T/C<42% is considered significant antitumor activity by the NCI. A T/C value<10% is considered to indicate highly significant antitumor activity, and is the level used by the NCI to justify a clinical trial if toxicity and certain other requirements are met (termed DN-2 level activity). A body weight loss nadir (mean of group) of greater than 20%, or greater than 20% of drug deaths are considered to indicate an excessively toxic dosage.

Statistical Analysis

Summary statistics, including mean and the standard error of the mean (SEM), are provided for the tumor volume of each group at each time point. Statistical analysis of difference in the tumor volume among the groups were conducted on the data obtained at the best therapeutic time point after the final dose. A one-way ANOVA was performed to compare the tumor volume and the tumor weight among groups, and when a significant F-statistics (a ratio of treatment variance to the error variance) was obtained, comparisons between groups were carried out with Games-Howell test. All data were analyzed using SPSS 17.0. $p<0.05$ is considered to be statistically significant.

Results

Figure 2:
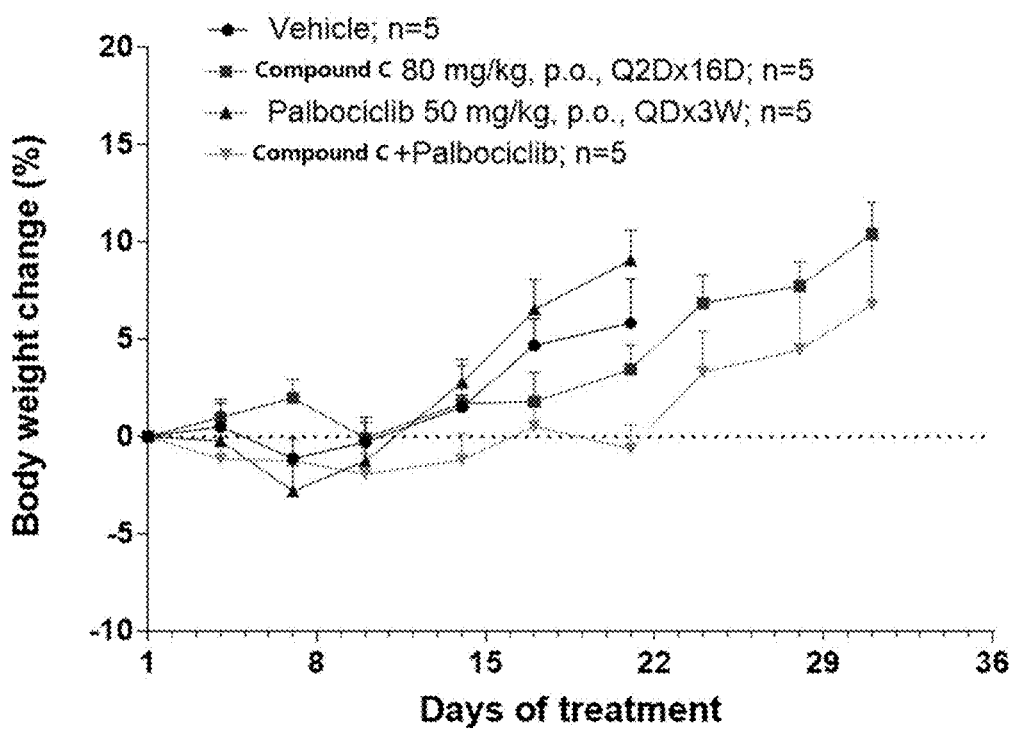
FIG. 2 shows body weight change (%) of mice bearing liposarcoma patient-derived xenograft tumors under the treatment with compound C and palbociclib (Mean±SEM) in embodiment 2.

Compound C was tested in combination with palbociclib in subcutaneous liposarcoma patient-derived xenograft in female Balb/c nude mice. As shown in FIG. 1 and Table 2, compound C given at 80 mg/kg p.o. for 16 days showed good activity against liposarcoma with a T/C value of 22% (P<0.01) on day 21. Palbociclib at 50 mg/kg (p.o., q.d×3w) had modest activities on tumor growth with a T/C value of 70% (P<0.05). However, compound C plus palbociclib demonstrated much greater antitumor activity with a T/C value of 7% (P<0.01). The synergy score was 2.21, which indicated that the combination treatment elicited synergistic effects. Two out of five mice showed partial response (PR) after the combination treatment. There was no significant change in body weight during all treatments as shown in FIG. 2.

TABLE 2

RTV, T/C (%) values and synergy scores at key time points

|  | RTV @D 21 | T/C (%) @D 21 | Synergy score @D 21 | Tumor status (response) @D 21 |
|---|---|---|---|---|
| Vehicle | 21.70 ± 2.50 | — | — | — |
| Compound C 80 mg/kg | 4.83 ± 1.56 *** | 22.28 | — | — |
| Palbociclib 50 mg/kg | 15.19 ± 1.31 ** | 70.00 | — | — |
| Compound C + Palbociclib | 1.53 ± 0.60 ***### | 7.04 | 2.21 | 2/5 PR |

Note:
Synergy score > 1, Synergistic; score = 1, Additive; score < 1, Antagonistic.
** $p < 0.01$ vs Vehicle group;
*** $p < 0.001$ vs Vehicle group;
$p < 0.001$ vs Palbociclib group;
PR: partial response.

Embodiment 3

Figure 3:
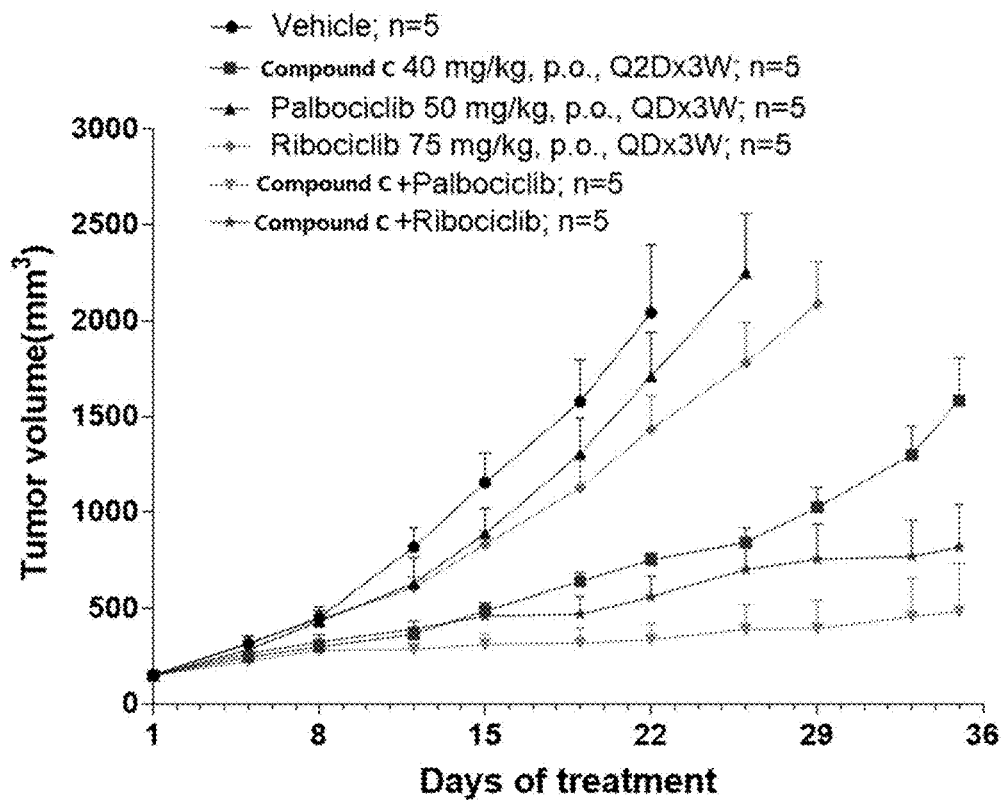
FIG. 3 shows antitumor activity of compound C as a single agent or in combination with palbociclib, ribociclib in the treatment of liposarcoma patient derived xenograft (Mean±SEM) in embodiment 3.
Figure 4:
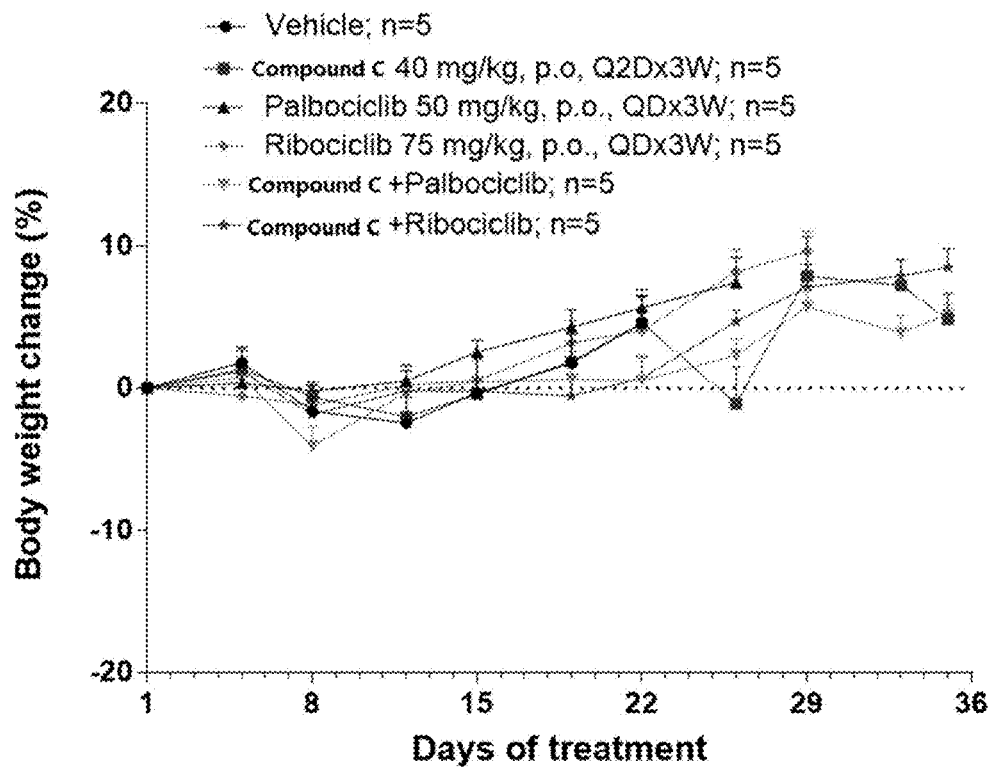
FIG. 4 shows body weight change (%) of mice bearing liposarcoma patient-derived xenograft tumors under the treatment with compound C, palbociclib, ribociclib or in combination (Mean±SEM) in embodiment 3.

Compound C was further tested with two CDK4/6 inhibitors, palbociclib and ribociclib in the same human liposarcoma patient-derived xenograft model as described in embodiment 1. As shown in FIG. 3 and Table 3, palbociclib at 50 mg/kg (p.o., q.d×3w) and ribociclib at 75 mg/kg (p.o., q.d×3w) had limited antitumor activities on tumor growth with a T/C value of 83.5% (P>0.05) and 71.7% (P>0.05), respectively. Compound C at 40 mg/kg (p.o., q.2d×3w) exhibited potent antitumor activity with a T/C value of 38.4% (P<0.05) on day 22. Combination treatments with compound C (40 mg/kg p.o., q.2d×3w) and palbociclib (50 mg/kg, p.o., q.d×3w) or ribociclib (75 mg/kg, p.o., q.d×3w) significantly inhibited tumor growth, with T/C values of 16.87% and 27.09% on day 22, respectively. Synergistic effects between compound C and palbociclib or ribociclib were demonstrated as synergy scores were larger than 1. Importantly, partial response occurred in two combination treatment groups. No significant body weight changes were observed during all treatments as shown in FIG. 4.

TABLE 3

RTV, T/C (%) values and synergy scores at key time points

|  | RTV @D 22 | T/C(%) @D 22 | Synergy @D 22 | RTV @35 | Tumor status (response) @33 |
|---|---|---|---|---|---|
| Vehicle | 13.63 ± 2.29 | — | — | — | |
| Compound C 40 mg/kg | 5.24 ± 0.61 | 38.44 | — | 10.95 ± 1.66 | |
| Palbociclib 50 mg/kg | 11.36 ± 0.96 | 83.50 | — | — | |

TABLE 3-continued

RTV, T/C (%) values and synergy scores at key time points

|  | RTV @D 22 | T/C(%) @D 22 | Synergy @D 22 | RTV @35 | Tumor status (response) @33 |
|---|---|---|---|---|---|
| Ribociclib 75 mg/kg | 9.77 ± 1.22 | 71.70 | — | — |  |
| Compound C + Palbociclib | 2.30 ± 0.63 \*\*### | 16.87 | 1.90 | 3.41 ± 1.82 | 1/5 PR |
| Compound C + Ribociclib | 3.69 ± 0.71 ++ | 27.09 | 1.02 | 5.26 ± 1.64 | 1/5 PR |

\*\* p < 0.05 vs Vehicle group;
### p < 0.001 vs Palbociclib group;
++ p < 0.05 vs Ribociclib group;
Synergy Ratio > 1, Synergistic; Ratio = 1, Additive; Ratio < 1, Antagonistic;
PR: partial response.

Embodiment 4

Compound C was further tested in combination with palbociclib in another patient-derived xenograft model (LU-01-0448 PDX model). LU-01-0448 PDX model was a subcutaneous lung cancer patient-derived xenograft model, which was established according to the procedures of LP-19-0029 PDX model in embodiment 2.

This experiment was carried out according to Table 4 and the procedures described in embodiment 2.

TABLE 4

Groups and dosing regimen

| Group | n | Treatment | Dose (mg/kg) | Dosing Route | Schedule |
|---|---|---|---|---|---|
| 1 | 2 | Compound C vehicle + Palbociclib vehicle | — | p.o. + p.o. | QD × 5 D + QD × 21 D |
| 2 | 2 | Compound C | 100 | p.o. | QD × 5 D |
| 3 | 2 | Palbociclib | 50 | p.o. | QD × 21 D |
| 4 | 2 | Compound C + Palbociclib | 100 + 50 | p.o. + p.o. | QD × 5 D + QD × 21 D |

Note:
n: animal number; QD: daily; p.o.: orally; QD: daily.

Figure 5:
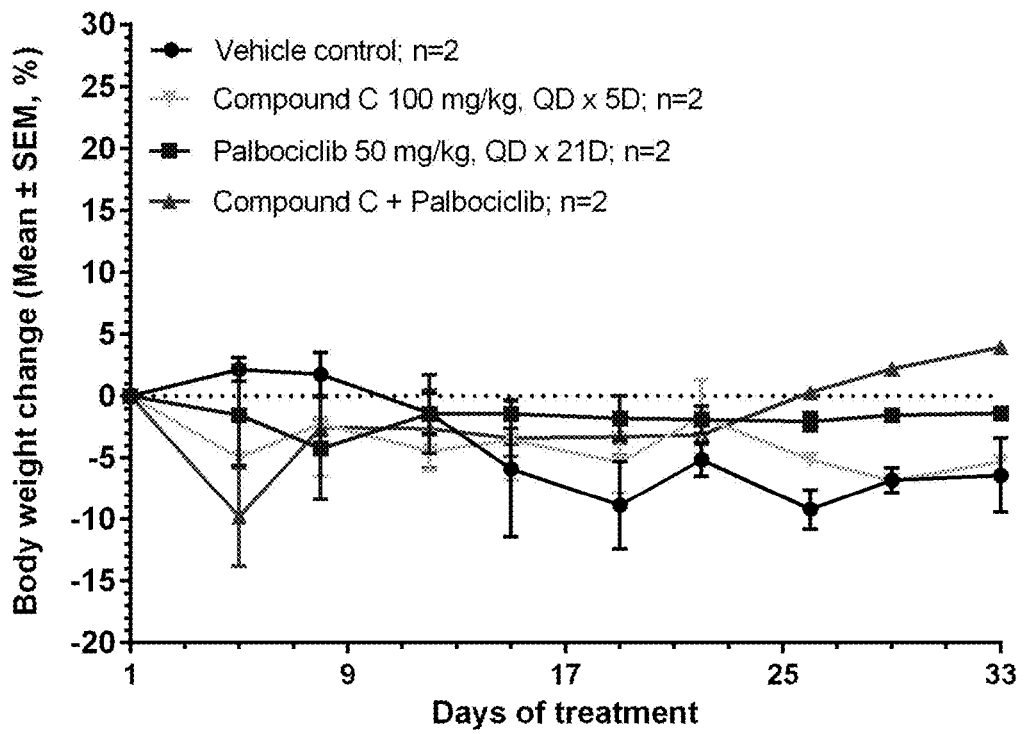
FIG. 5 shows body weight change (%) of mice bearing lung cancer patient-derived xenograft tumors under the treatment with compound C, palbociclib or in combination (Mean±SEM) in embodiment 4.
Figure 6:
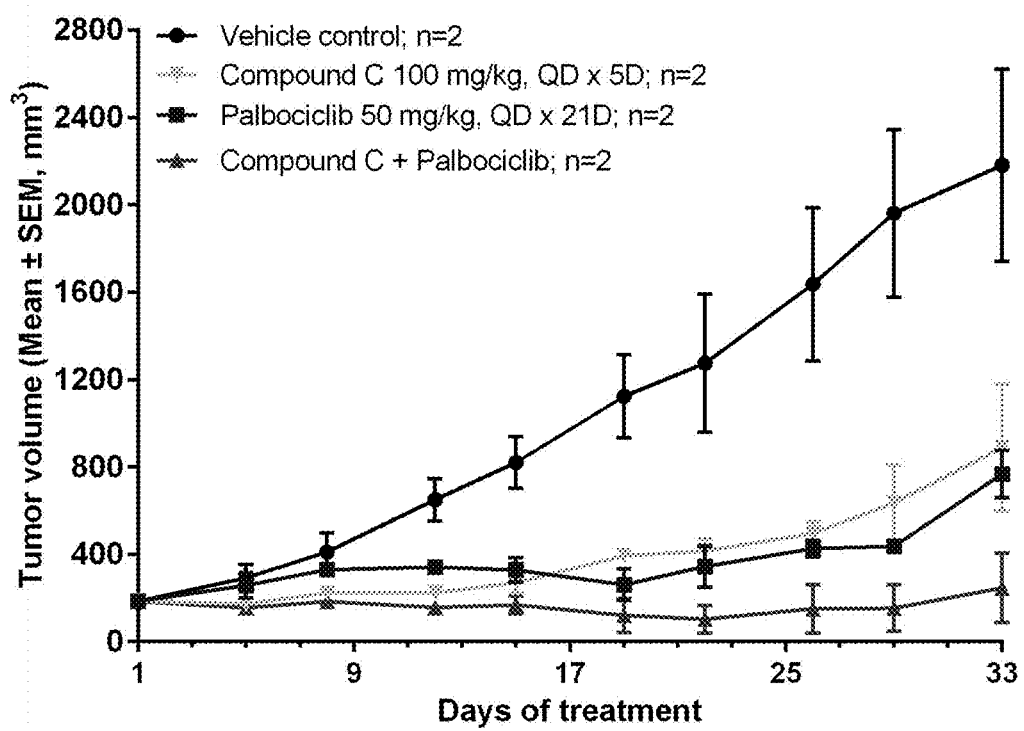
FIG. 6 shows antitumor activity of compound C as a single agent or in combination with palbociclib in the treatment of lung cancer patient derived xenograft (Mean±SEM) in embodiment 4.

As shown in FIG. 5, there was no significant change in body weight during all treatments. As shown in FIG. 6, combination treatments with compound C and palbociclib significantly inhibited tumor growth, with T/C value of 11.30% on day 33. Synergistic effects between compound C and palbociclib were demonstrated as synergy scores were larger than 1, as shown in Table 5.

TABLE 5

RTV, T/C (%) values and synergy score at key time points

| Treatment | RTV @ D 33 | T/C(%) @ D 33 | Synergy score @ D 33 | mRECIST | Response @ D 33 |
|---|---|---|---|---|---|
| Vehicle control | 11.72 ± 2.12 | — | — | 2/2 PD | 2/2 PD |
| Compound C | 4.85 ± 1.85 | 41.43 | — | 2/2 SD | 2/2 PD |
| Palbociclib | 4.18 ± 0.80 | 35.71 | — | 2/2 PD | 2/2 PD |

TABLE 5-continued

RTV, T/C (%) values and synergy score at key time points

| Treatment | RTV @ D 33 | T/C(%) @ D 33 | Synergy score @ D 33 | mRECIST | Response @ D 33 |
|---|---|---|---|---|---|
| Compound C + Palbociclib | 1.32 ± 0.84 | 11.30 | 1.31 | 1/2 PR, 1/2SD | 1/2 PR, 1/2PD |

Note:
Synergy score > 1, synergistic; score = 1, additive; score < 1, Antagonistic.
PD: progressive disease; SD: stable disease; PR: partial response.

It is to be understood that the foregoing description of the preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:
1. A pharmaceutical composition comprising
   (i) a compound of formula (I) or a pharmaceutically acceptable salt thereof; and,
   (ii) a CDK inhibitor or a pharmaceutically acceptable salt thereof;

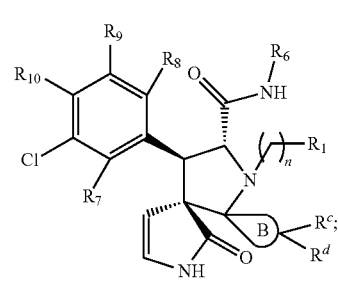

I

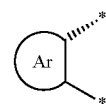

is selected from the group consisting of

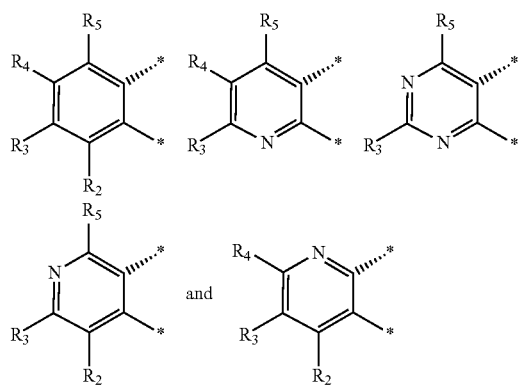

B is a $C_{4-7}$ carbocyclic ring;
$R_1$ is H, unsubstituted $C_{1-4}$ alkyl, unsubstituted $C_{3-8}$ cycloalkyl, unsubstituted 4 to 12-membered heterocycloalkyl, $OR^a$, or $NR^aR^b$; the heteroatom of the heterocycloalkyl is independently selected from nitrogen, oxygen, and sulfur, the number of the heteroatom is 1-4;
n is 0, 1, or 2;
$R_2$, $R_3$, $R_4$, $R_5$, $R_7$, $R_8$, $R_9$, and $R_{10}$ are independently selected from the group consisting of H, F, Cl, $CH_3$, and $CF_3$;
$R_6$ is

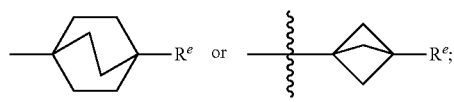

each of $R^a$ is independently H or unsubstituted $C_{1-4}$ alkyl;
each of $R^b$ is independently H or unsubstituted $C_{1-4}$ alkyl;
$R^c$ and $R^d$ are substituents on one carbon atom of ring B, wherein
$R^c$ is H, $C_{1-3}$ alkyl, $C_{1-3}$ alkylene-$OR^a$, $OR^a$, or halo;
$R^d$ is H, $C_{1-3}$ alkyl, $C_{1-3}$ alkylene-$OR^a$, $OR^a$, or halo; or
$R^c$ and $R^d$ are taken together with the carbon to which they are attached to form a 4 to 6-membered spiro carbocyclic substituent, optionally containing an oxygen atom; and
$R^e$ is —C(=O)$OR^a$, —C(=O)$NR^aR^b$, —C(=O)NHSO$_2$CH$_3$.

2. The pharmaceutical composition of claim 1, wherein, the compound of formula (I) is Compound Q

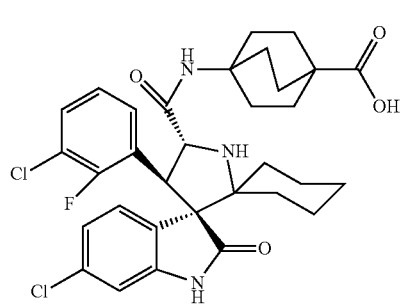

Compound M

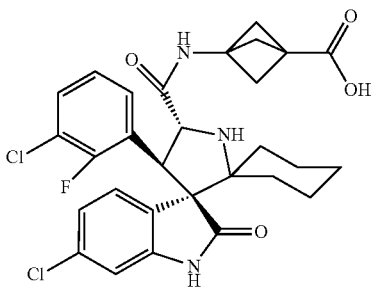

Compound N

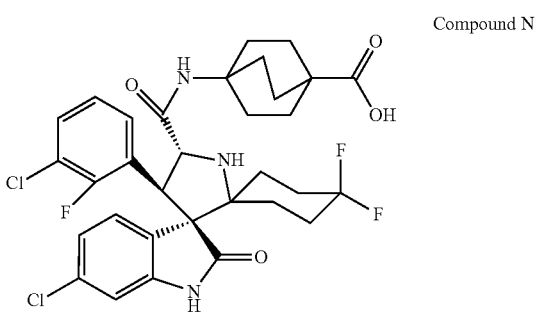

Compound H

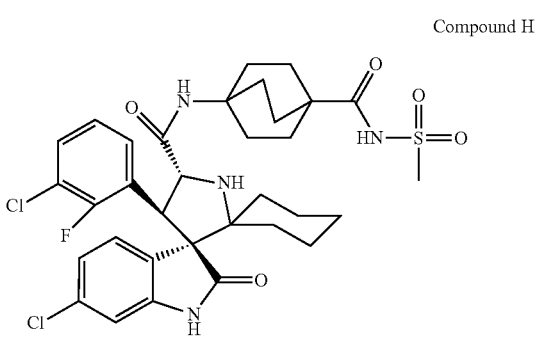

Compound J

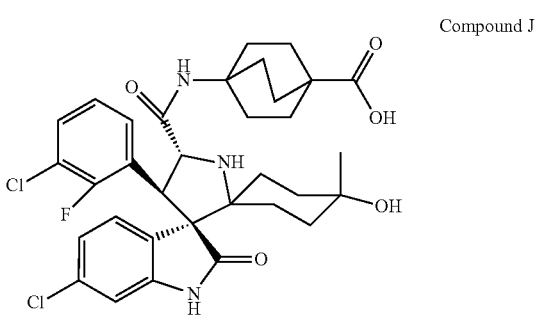

Compound G

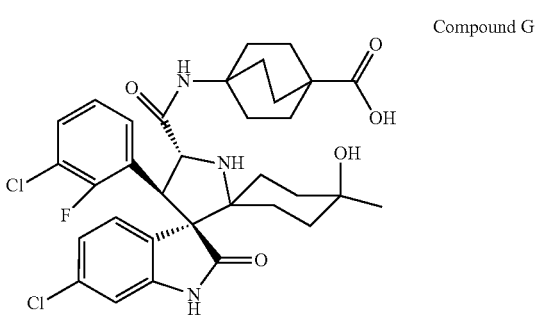

Compound E
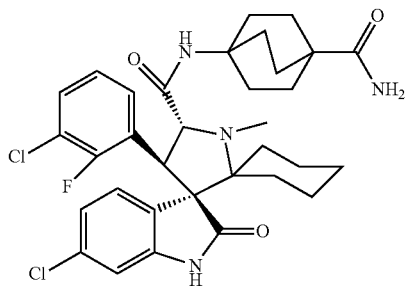

Compound C
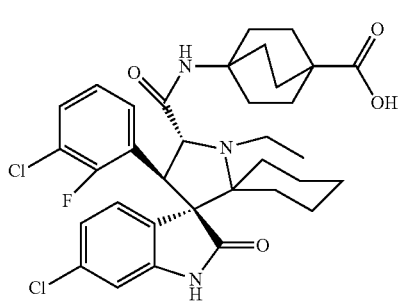

Compound F
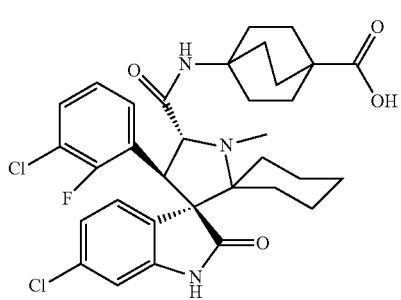

Compound Y
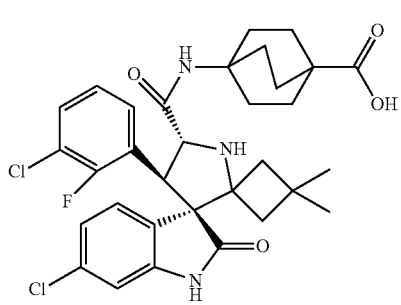

Compound K
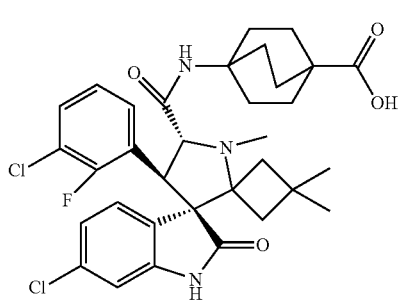

Compound P
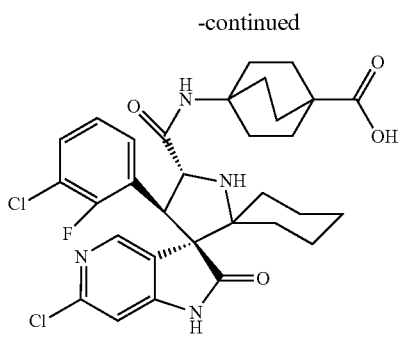

Compound T
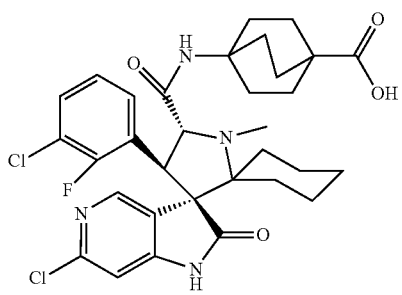

Compound S
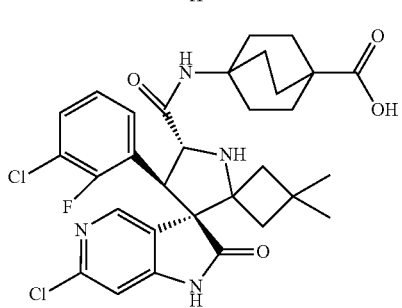

Compound W
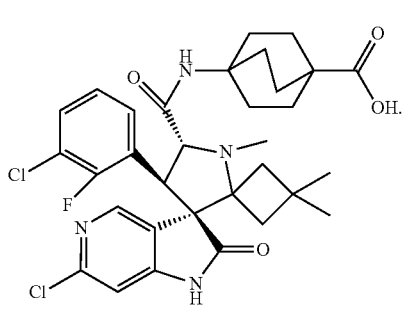

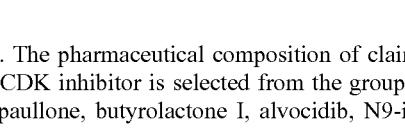

3. The pharmaceutical composition of claim 1, wherein, the CDK inhibitor is selected from the group consisting of kenpaullone, butyrolactone I, alvocidib, N9-isopropyl-olomoucine, indirubin-3'-monoxime, NU2058, olomoucine II, 9-cyanopaullone, 5-iodo-indirubin-3'-monoxime, NU6102, oxindole I, SU 9516, roscovitine, RO-3306, 10Z-hymenialdisine, AZD 5438, AT7519, AT7519 HCL, dinaciclib, R547, CGP 74514A, SNS-032, XL413, BMS-265246, JNJ-7706621, PHA-793887, P276-00, PHA-767491, milciclib, NU6027, LDC000067, LDC4297, MK-8776, Atuveciclib, Skp2 inhibitor C1, BS-181-HCL, THZ1 2HC1, Senexin A, MSC2530818, Wogonin, Purvalanol A, LY2857785, K03861, ML167, ON123300, ribociclib, palbociclib, and abemaciclib.

4. The pharmaceutical composition of claim 1, wherein, the CDK inhibitor is an inhibitor of CDK4 or CDK6.

5. The pharmaceutical composition of claim 1, wherein, the compound of formula (I) is Compound C

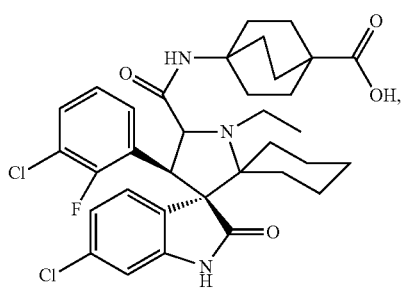

or a pharmaceutically acceptable salt thereof;
or, the CDK inhibitor is compound A or compound B, or a pharmaceutically acceptable salt thereof;

Compound A

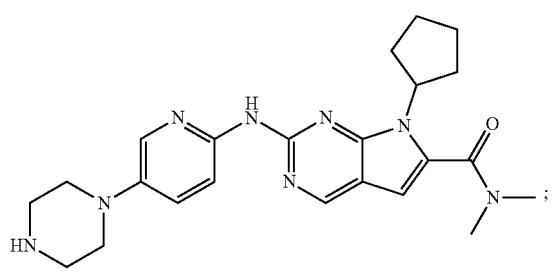

Compound B

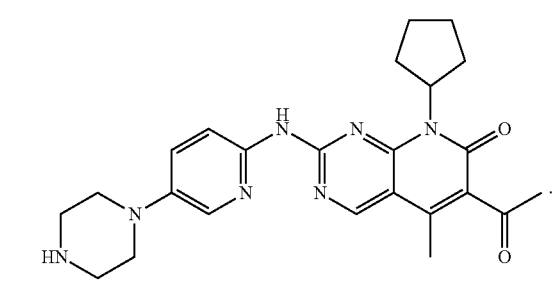

6. The pharmaceutical composition of claim 5, wherein, the compound of formula (I) is Compound C

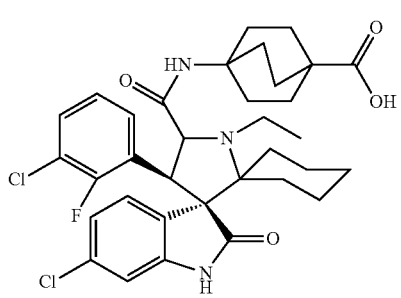

or a pharmaceutically acceptable salt thereof, and, the CDK inhibitor is compound A or a pharmaceutically acceptable salt thereof.

7. The pharmaceutical composition of claim 5, wherein, the compound of formula (I) is Compound C

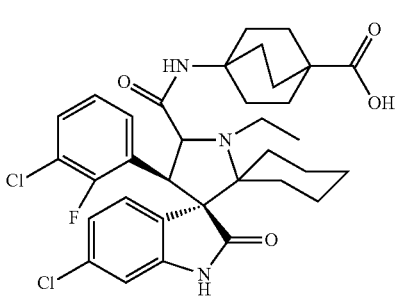

or a pharmaceutically acceptable salt thereof, and, the CDK inhibitor is compound B or a pharmaceutically acceptable salt thereof.

8. The pharmaceutical composition of claim 1, wherein, the weight ratio of the compound of formula (I) to the CDK inhibitor is 50:1 to 1:50.

9. A method for the treatment of a cancer, which comprises administering to a subject in need thereof a therapeutically effective amount of a compound of formula (I) or a pharmaceutically acceptable salt thereof, and a therapeutically effective amount of a CDK inhibitor or a pharmaceutically acceptable salt thereof:

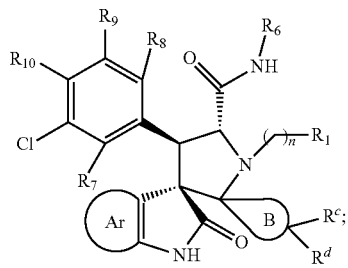

I

is selected from the group consisting of

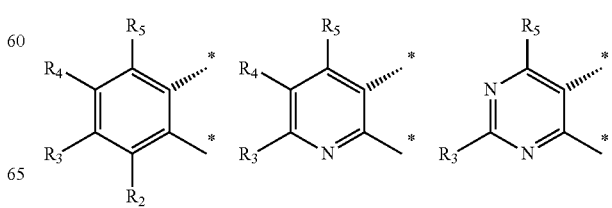

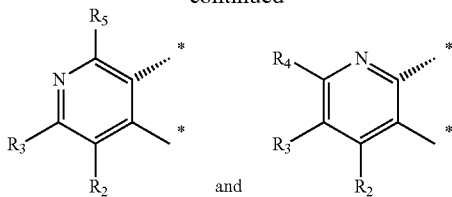

and

B is a $C_{4-7}$ carbocyclic ring;

$R_1$ is H, unsubstituted $C_{1-4}$ alkyl, unsubstituted $C_{3-8}$ cycloalkyl, unsubstituted 4 to 12-membered heterocycloalkyl, $OR^a$, or $NR^aR^b$; the heteroatom of the heterocycloalkyl is independently selected from nitrogen, oxygen, and sulfur, the number of the heteroatom is 1-4;

n is 0, 1, or 2;

$R_2$, $R_3$, $R_4$, $R_5$, $R_7$, $R_8$, $R_9$ and $R_{10}$ are independently selected from the group consisting of H, F, Cl, $CH_3$, and $CF_3$;

$R_6$ is

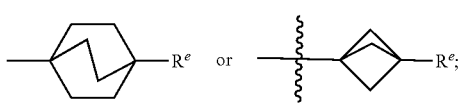

each of $R^a$ is independently H or unsubstituted $C_{1-4}$ alkyl;
each of $R^b$ is independently H or unsubstituted $C_{1-4}$ alkyl;
$R^c$ and $R^d$ are substituents on one carbon atom of ring B, wherein
$R^c$ is H, $C_{1-3}$ alkyl, $C_{1-3}$ alkylene-$OR^a$, $OR^a$, or halo;
$R^d$ is H, $C_{1-3}$ alkyl, $C_{1-3}$ alkylene-$OR^a$, $OR^a$, or halo; or
$R^c$ and $R^d$ are taken together with the carbon to which they are attached to form a 4 to 6-membered spiro carbocyclic substituent, optionally containing an oxygen atom; and
$R^e$ is —C(=O)$OR^a$, —C(=O)$NR^aR^b$, or —C(=O)NHSO$_2$CH$_3$; and
wherein the cancer is liposarcoma or lung cancer.

10. A kit comprising separate containers in a single package: in one container a pharmaceutical composition comprising a compound of formula (I) or a pharmaceutically acceptable salt thereof, and in a second container a pharmaceutical composition comprising a CDK inhibitor or a pharmaceutically acceptable salt thereof:

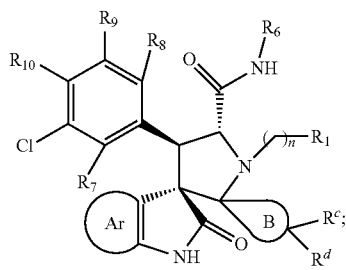

I

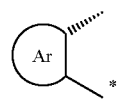

is selected from the group consisting of

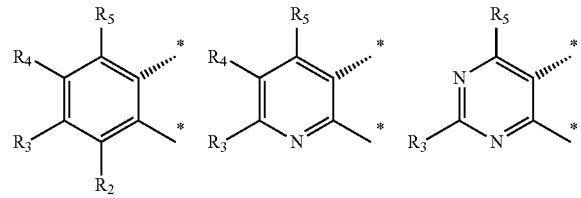

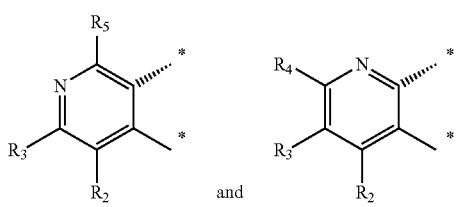

and

B is a $C_{4-7}$ carbocyclic ring;

$R_1$ is H, unsubstituted $C_{1-4}$ alkyl, unsubstituted $C_{3-8}$ cycloalkyl, unsubstituted 4 to 12-membered heterocycloalkyl, $OR^a$, or $NR^aR^b$; the heteroatom of the heterocycloalkyl is independently selected from nitrogen, oxygen, and sulfur, the number of the heteroatom is 1-4;

n is 0, 1, or 2;

$R_2$, $R_3$, $R_4$, $R_5$, $R_7$, $R_8$, $R_9$ and $R_{10}$ are independently selected from the group consisting of H, F, Cl, $CH_3$, and $CF_3$;

$R_6$ is

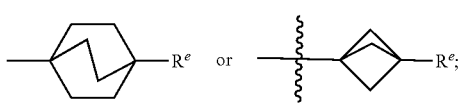

each of $R^a$ is independently H or unsubstituted $C_{1-4}$ alkyl;
each of $R^b$ is independently H or unsubstituted $C_{1-4}$ alkyl;
$R^c$ and $R^d$ are substituents on one carbon atom of ring B, wherein
$R^c$ is H, $C_{1-3}$ alkyl, $C_{1-3}$ alkylene-$OR^a$, $OR^a$, or halo;
$R^d$ is H, $C_{1-3}$ alkyl, $C_{1-3}$ alkylene-$OR^a$, $OR^a$, or halo; or
$R^c$ and $R^d$ are taken together with the carbon to which they are attached to form a 4 to 6-membered spiro carbocyclic substituent, optionally containing an oxygen atom; and
$R^e$ is —C(=O)$OR^a$, —C(=O)$NR^aR^b$, or —C(=O)NHSO$_2$CH$_3$.

11. The pharmaceutical composition of claim 1, wherein the compound of formula (I) is

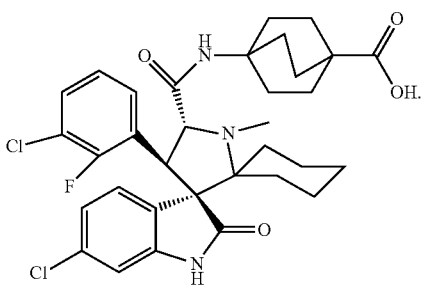

Compound F

12. The pharmaceutical composition of claim 1, wherein the compound of formula (I) is

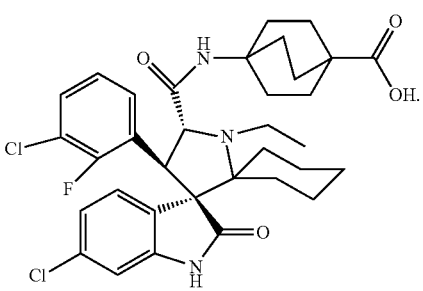

Compound C

13. The method of claim 9, wherein the cancer is liposarcoma.

14. The method of claim 13, wherein the liposarcoma is well-differentiated liposarcoma.

15. The method of claim 13, wherein the liposarcoma is dedifferentiated liposarcoma.

16. The method of claim 9, wherein the cancer is lung cancer.

17. The method of claim 16, wherein lung cancer is non-small cell lung cancer.

18. The method of claim 9, wherein the compound of formula (I) and the CDK inhibitor are administered simultaneously.

19. The method of claim 9, wherein the compound of formula (I) and the CDK inhibitor are administered separately.

20. The method of claim 9, wherein the compound of formula (I) is

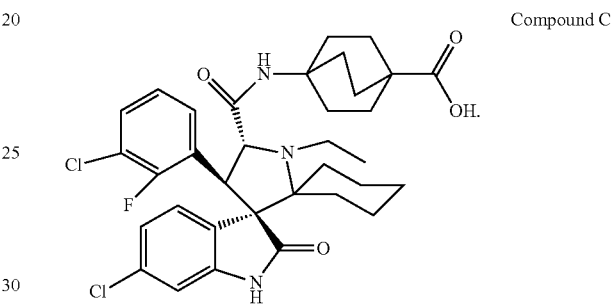

Compound C

* * * * *

UNITED STATES PATENT AND TRADEMARK OFFICE
CERTIFICATE OF CORRECTION

PATENT NO. : 11,452,716 B2  
APPLICATION NO. : 16/896059  
DATED : September 27, 2022  
INVENTOR(S) : Dajun Yang et al.

Page 1 of 2

It is certified that error appears in the above-identified patent and that said Letters Patent is hereby corrected as shown below:

In the Claims

In Column 24, Lines 50–60 (Claim 1), replace the chemical structure of Formula (I) with:

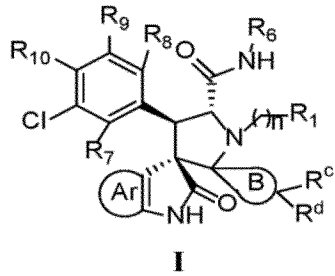

In Column 28, Line 25 (Claim 2), insert the term --, or-- after "Compound S"

In Column 29, Lines 1–15 (Claim 5), replace the chemical structure of Compound C with:

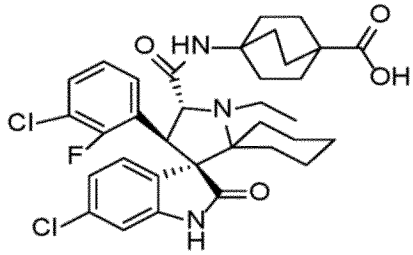

Compound C

Signed and Sealed this  
Twenty-second Day of November, 2022

Katherine Kelly Vidal  
*Director of the United States Patent and Trademark Office*

In Column 29, Lines 50–60 (Claim 6), replace the chemical structure of Compound C with:
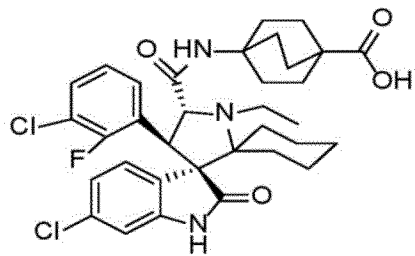
Compound C
In Column 30, Lines 5–15 (Claim 7), replace the chemical structure of Compound C with:
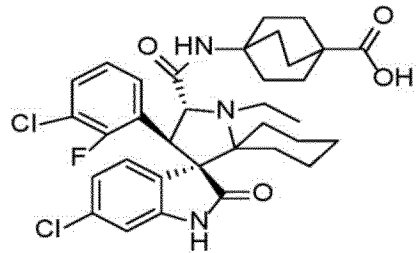
Compound C